(12) United States Patent
Reever

(10) Patent No.: US 8,123,705 B2
(45) Date of Patent: Feb. 28, 2012

(54) ADJUSTABLE PROFILE PROBE

(75) Inventor: Kenneth P. Reever, Hopedale, MA (US)

(73) Assignee: Boston Scientific Scimed, Inc., Natick, MA (US)

( * ) Notice: Subject to any disclaimer, the term of this patent is extended or adjusted under 35 U.S.C. 154(b) by 976 days.

(21) Appl. No.: 11/246,936

(22) Filed: Oct. 6, 2005

(65) Prior Publication Data

US 2007/0093880 A1    Apr. 26, 2007

(51) Int. Cl.
*A61B 5/103* (2006.01)
*A61B 5/117* (2006.01)

(52) U.S. Cl. ........................................ 600/593

(58) Field of Classification Search .................. 600/459, 600/462, 463, 549, 593, 587, 591; 607/100
See application file for complete search history.

(56) References Cited

U.S. PATENT DOCUMENTS

| | | | |
|---|---|---|---|
| 4,046,139 A | 9/1977 | Horn | |
| 4,311,154 A | 1/1982 | Sterzer et al. | |
| 4,566,465 A * | 1/1986 | Arhan et al. | 600/591 |
| 4,813,429 A | 3/1989 | Eshel et al. | |
| 5,106,360 A * | 4/1992 | Ishiwara et al. | 600/2 |
| 5,300,099 A | 4/1994 | Rudie | |
| 5,330,518 A | 7/1994 | Neilson et al. | |
| 5,335,669 A | 8/1994 | Tihon et al. | |
| 5,370,677 A | 12/1994 | Rudie et al. | |
| 5,385,544 A | 1/1995 | Edwards et al. | |
| 5,404,881 A | 4/1995 | Cathaud et al. | |
| 5,413,588 A | 5/1995 | Rudie et al. | |
| 5,464,437 A | 11/1995 | Reid et al. | |
| 5,464,445 A | 11/1995 | Rudie et al. | |
| 5,545,137 A | 8/1996 | Rudie et al. | |
| 5,575,811 A | 11/1996 | Reid et al. | |
| 5,620,480 A | 4/1997 | Rudie | |
| 5,628,770 A | 5/1997 | Thome et al. | |
| 5,643,335 A | 7/1997 | Reid et al. | |
| 5,645,528 A | 7/1997 | Thome | |
| 5,733,319 A | 3/1998 | Neilson et al. | |
| 5,755,754 A | 5/1998 | Rudie et al. | |
| 5,792,070 A | 8/1998 | Kauphusman et al. | |
| 5,800,486 A | 9/1998 | Thome et al. | |
| 5,807,395 A | 9/1998 | Mulier et al. | |

(Continued)

OTHER PUBLICATIONS

Seven page *International Preliminary Report on Patentability* dated Apr. 17, 2008 and from corresponding PCT patent application No. PCT/US2006/030100.

(Continued)

*Primary Examiner* — Max Hindenburg
*Assistant Examiner* — Adam Eiseman
(74) *Attorney, Agent, or Firm* — Brown Rudnick LLP

(57) ABSTRACT

An adjustable profile probe for insertion in a body cavity to sense a biological parameter includes an elongated shaft having a sensor panel and a resiliently expandable portion substantially opposing the sensor panel. An expansion mechanism is at least partially housed within the elongated shaft for varying the profile of the probe. The expansion mechanism includes a base plate adjacent to the resiliently expandable portion and a plurality of lever arms pivotally mounted to the base plate and the sensor panel. An actuating member pivotally connects to the lever arms such that upon movement of the actuating member, the resiliently expandable portion is selectively collapsed or expanded by the plurality of lever arms pivoting between a minimal profile position near parallel with the elongated shaft and an expanded profile position with the lever arms being near perpendicular to the elongated shaft.

17 Claims, 6 Drawing Sheets

U.S. PATENT DOCUMENTS

| | | | |
|---|---|---|---|
| 5,843,144 | A | 12/1998 | Rudie et al. |
| 5,865,788 | A | 2/1999 | Edwards et al. |
| 5,879,295 | A | 3/1999 | Li et al. |
| 5,899,932 | A | 5/1999 | Dann et al. |
| 5,916,240 | A | 6/1999 | Rudie et al. |
| 5,916,241 | A | 6/1999 | Rudie et al. |
| 5,931,860 | A | 8/1999 | Reid et al. |
| 5,938,692 | A | 8/1999 | Rudie |
| 5,964,791 | A | 10/1999 | Bolmsjo |
| 5,987,360 | A | 11/1999 | McGrath et al. |
| 6,007,571 | A | 12/1999 | Neilson et al. |
| 6,009,351 | A | 12/1999 | Flachman |
| 6,032,078 | A | 2/2000 | Rudie |
| 6,036,631 | A | 3/2000 | McGrath et al. |
| 6,059,078 | A | 5/2000 | Nykoluk |
| 6,067,475 | A | 5/2000 | Graves et al. |
| 6,119,045 | A | 9/2000 | Bolmsjo |
| 6,122,551 | A | 9/2000 | Rudie et al. |
| 6,123,083 | A | 9/2000 | McGrath et al. |
| 6,135,968 | A | 10/2000 | Brounstein |
| 6,142,993 | A | 11/2000 | Whayne et al. |
| 6,148,236 | A | 11/2000 | Dann |
| 6,161,049 | A | 12/2000 | Rudie et al. |
| 6,216,703 | B1 | 4/2001 | Manker et al. |
| 6,272,384 | B1 | 8/2001 | Simon et al. |
| 6,312,391 | B1 | 11/2001 | Ramadhyani et al. |
| 6,348,039 | B1 | 2/2002 | Flachman et al. |
| 6,366,818 | B1 | 4/2002 | Bolmsjo |
| 6,402,742 | B1 | 6/2002 | Blewett et al. |
| 6,419,653 | B2 | 7/2002 | Edwards et al. |
| 6,440,127 | B2 | 8/2002 | McGovern et al. |
| 6,445,957 | B1 | 9/2002 | Bolmsjo |
| 6,447,505 | B2 | 9/2002 | McGovern et al. |
| 6,475,140 | B1 | 11/2002 | Konstorum et al. |
| 6,477,426 | B1 | 11/2002 | Fenn et al. |
| 6,490,488 | B1 | 12/2002 | Rudie et al. |
| 6,496,737 | B2 | 12/2002 | Rudie et al. |
| 6,497,704 | B2 | 12/2002 | Ein-Gal |
| 6,522,931 | B2 | 2/2003 | Manker et al. |
| 6,524,270 | B1 | 2/2003 | Bolmsjo et al. |
| 6,547,788 | B1 | 4/2003 | Maguire et al. |
| 6,584,361 | B1 | 6/2003 | Bolmsjo |
| 6,592,579 | B2 | 7/2003 | Arndt et al. |
| 6,596,017 | B1 | 7/2003 | Bolmsjo |
| 6,626,876 | B1 | 9/2003 | Bolmsjo et al. |
| 6,640,138 | B1 | 10/2003 | Schefermeyer et al. |
| RE38,299 | E | 11/2003 | Bolmsjo |
| 6,673,079 | B1 | 1/2004 | Kane |
| 6,692,493 | B2 | 2/2004 | McGovern et al. |
| 6,712,759 | B2 | 3/2004 | Muller |
| 6,740,108 | B1 | 5/2004 | Just et al. |
| 6,743,226 | B2 | 6/2004 | Cosman et al. |
| 6,758,857 | B2 | 7/2004 | Cioanta et al. |
| 6,788,977 | B2 | 9/2004 | Fenn et al. |
| 6,852,091 | B2 | 2/2005 | Edwards et al. |
| 6,852,105 | B2 | 2/2005 | Bolmsjo et al. |
| 6,868,290 | B2 | 3/2005 | Bolmsjo |
| 6,895,282 | B2 | 5/2005 | Gellman et al. |
| 2002/0010502 | A1 | 1/2002 | Trachtenberg et al. |
| 2002/0077552 | A1 | 6/2002 | Edwardsen et al. |
| 2003/0083574 | A1 | 5/2003 | Svaasand et al. |
| 2003/0111234 | A1 | 6/2003 | McClurkin et al. |
| 2003/0130575 | A1 | 7/2003 | Desai |
| 2003/0191513 | A1 | 10/2003 | Manker et al. |
| 2004/0077944 | A1 | 4/2004 | Steinberg et al. |
| 2004/0176699 | A1 | 9/2004 | Walker et al. |
| 2005/0010203 | A1 | 1/2005 | Edwards et al. |
| 2005/0085726 | A1 | 4/2005 | Lacoste et al. |

OTHER PUBLICATIONS

Medtronic website, Medtronic TUNA, www.medtronic.com/neuro/tuna, Sep. 16, 2005 (2 pages).

Johnson & Johnson Gateway website, "Optimize your Practice", www.jnj.lt/home.jhtml;jsessionid=WTZXE0PKGIYNICQ..., Sep. 16, 2005 (2 pages).

"Comparing Select Enlarged Prostate (BPH) Treatments", www.enlargedprostateinfo.com Sep. 16, 2005 (3 pages).

Urologix Website, "The Targis System: Optimal Durability and Enhanced Patient Comfort", www.urologix.com/uro_Targis.html , Sep. 16, 2005 (2 pages).

Urologix Website, "The Prostatron System: Fully Automated Treatment in only 30 Minutes", www.urologix.com/uro.html , Sep. 16, 2005 (2 pages).

ACMI Website, CoreTherm Microwave Thermotherapy System: A Treatment as Individual as Your Patients, www.acmicorp.com, Sep. 16, 2005 (2 pages).

Three-page International Search Report for corresponding PCT/US 06/30100.

Six-page Written Opinion for corresponding PCT/US 06/30100.

* cited by examiner

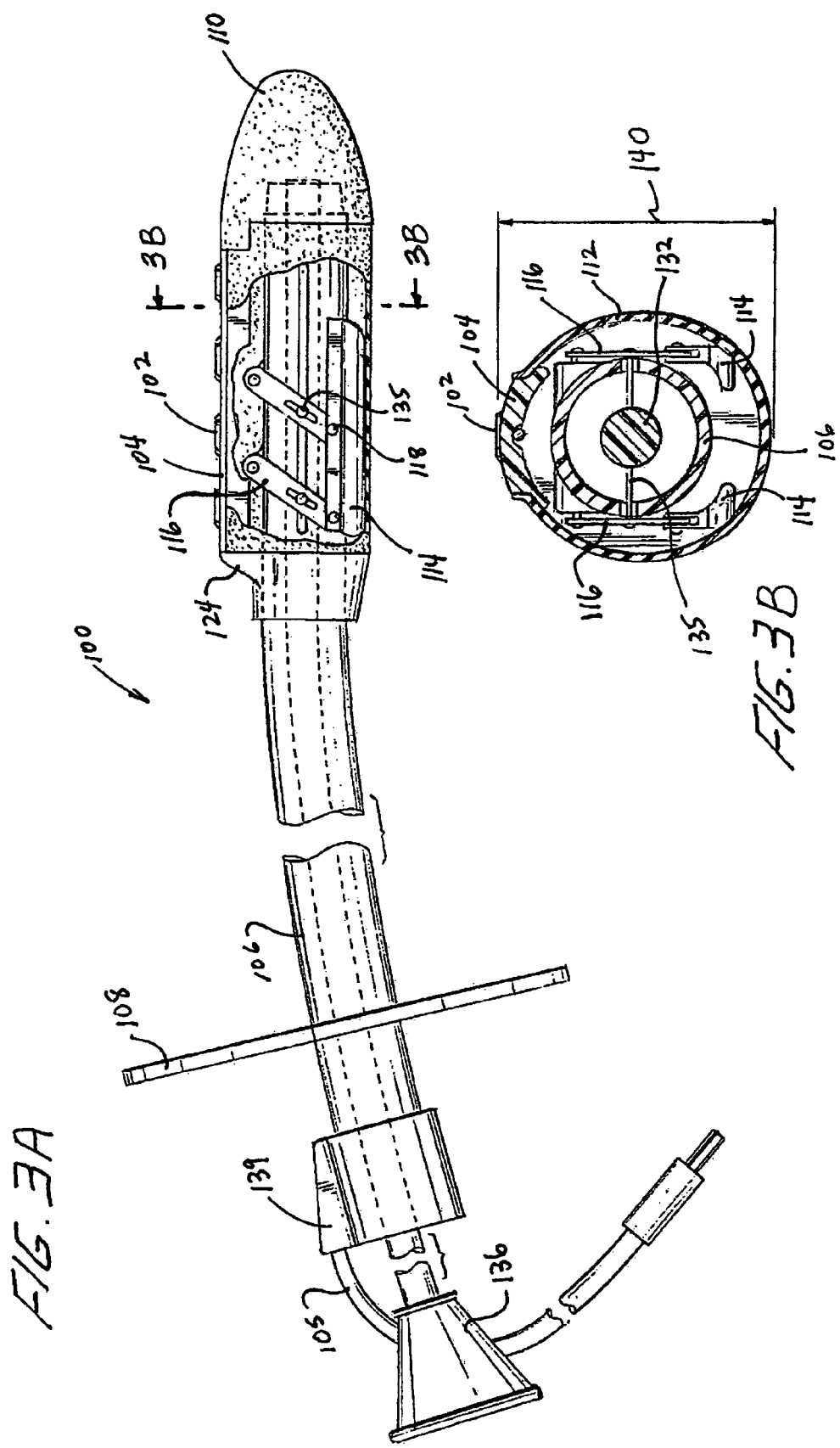

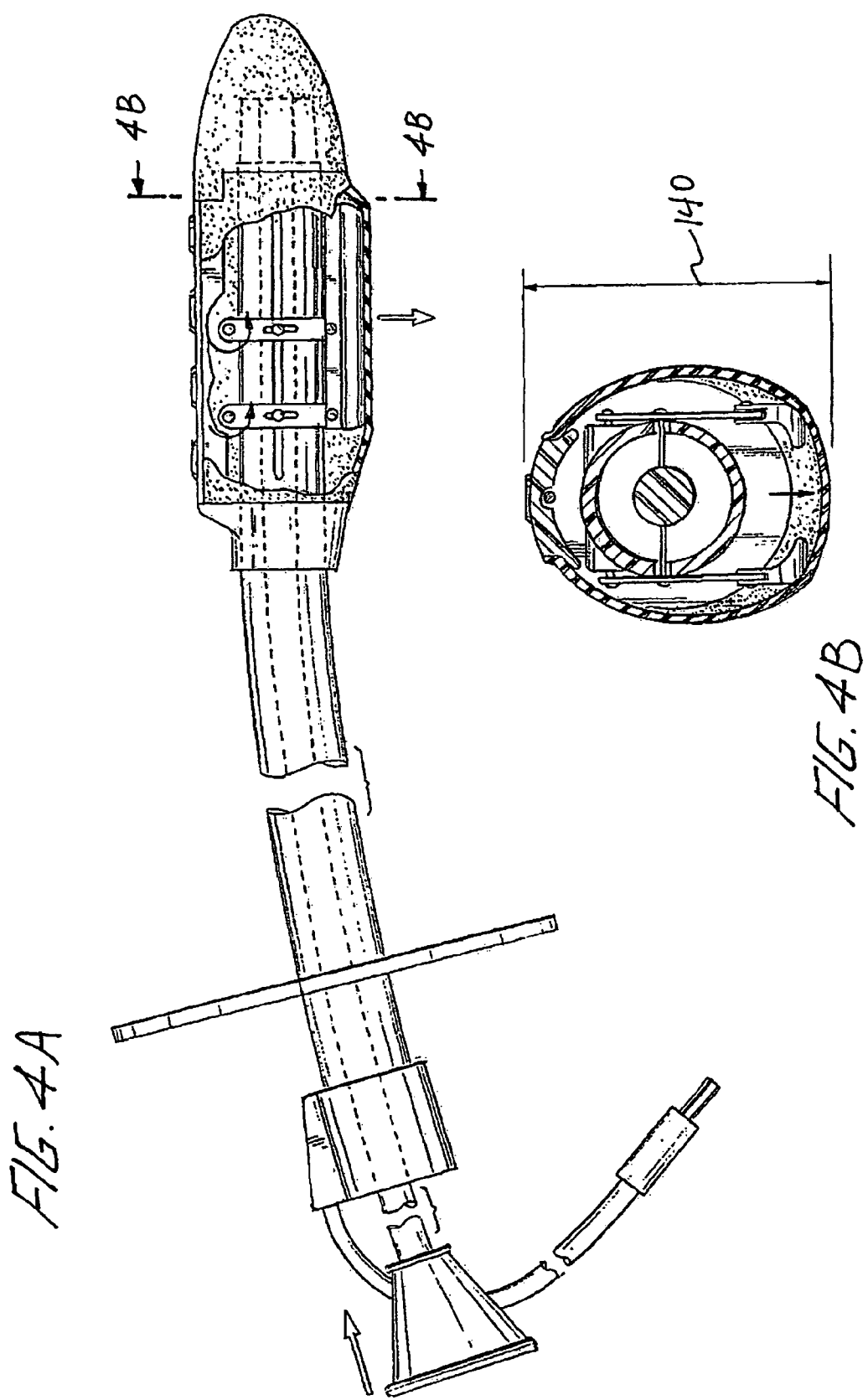

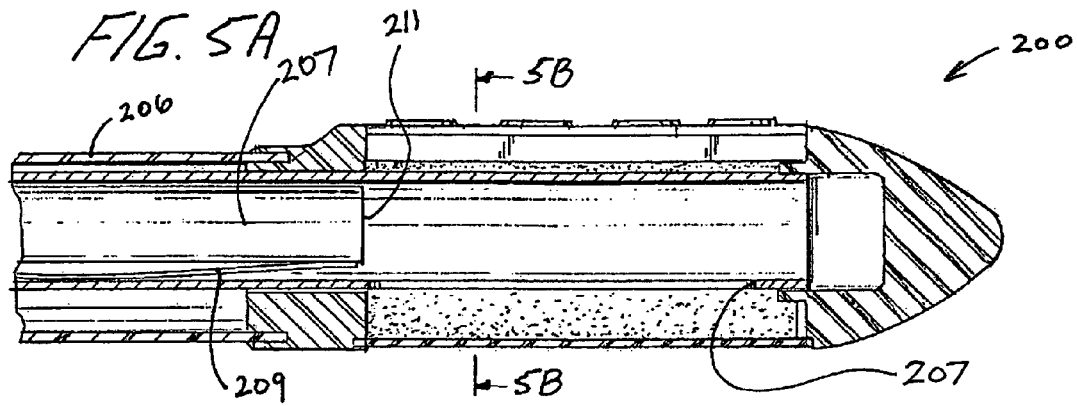
FIG. 5A
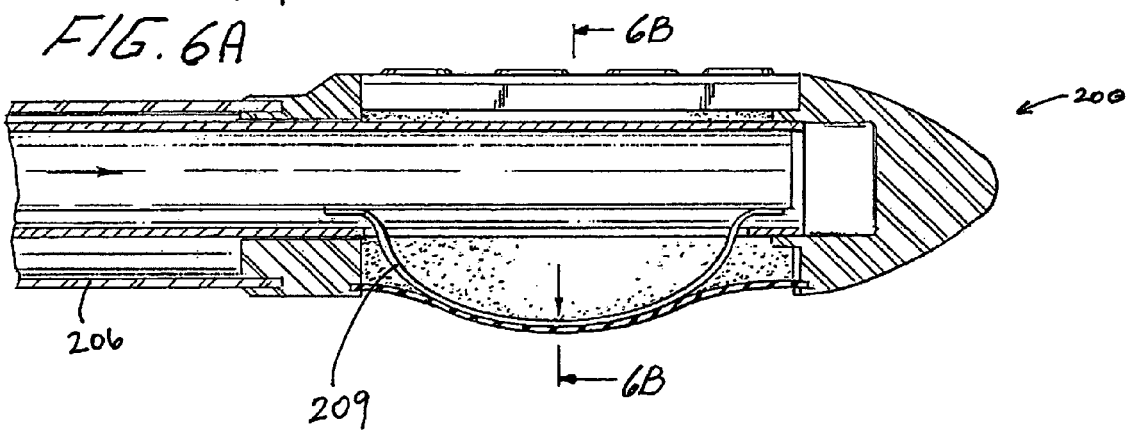
FIG. 6A
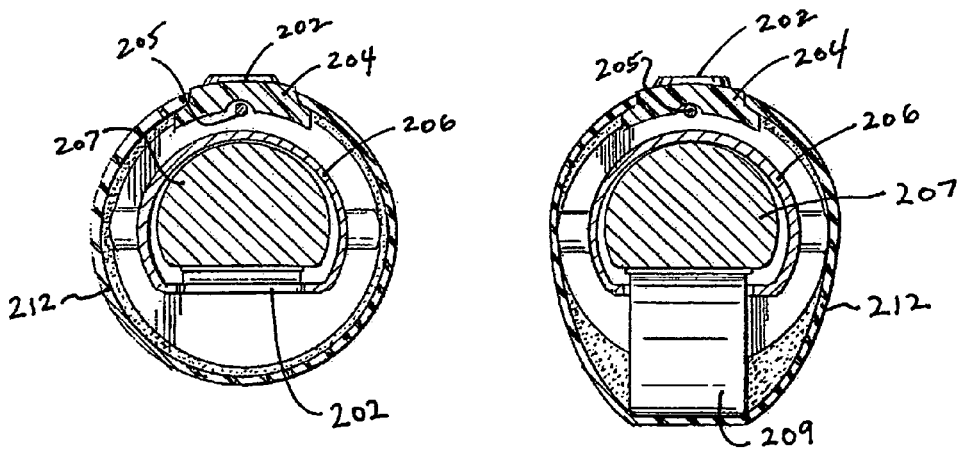
FIG. 5B
FIG. 6B

ADJUSTABLE PROFILE PROBE

TECHNICAL FIELD

The disclosed technology generally relates to monitoring a biological parameter after insertion of a medical device or a portion of the medical device into a body cavity and, more particularly, to a probe with an adjustable profile to allow collapsing for more comfortable and easier insertion into the body cavity and then expansion after placement within the body cavity.

BACKGROUND INFORMATION

The prostate gland is part of the male reproductive system. It consists of two lobes in front of the rectum and just below the bladder. The prostate gland also surrounds the urethra, the canal through which urine passes out of the body. The prostate gland has two main periods of growth. The first growth period is during puberty. However, during a man's mid-twenties, the prostate gland begins to grow again and continues to do so for the remainder of life. As the prostate gland grows, several problems often occur as a result of excessive growth. Rarely do such afflictions occur before forty, but as a man's age increases, the likelihood of prostate gland afflictions increases significantly.

Benign Prostate Hyperplasia (BPH) is the later growth of the prostate gland causing symptoms such as pain, frequent urination and inability to drain the bladder. Fortunately, a digital rectal exam can often lead to early detection of BPH and several effective treatment modalities exist. For example, drugs such as finasteride, transurethral microwave procedures, transurethral needle ablation, and surgical treatments are available.

Several approaches to treatment by heating the prostate are known. See, for example, U.S. Pat. Nos. 6,477,426, 6,592,579, 6,402,742, 6,142,993, 5,865,788, 5,385,544, 6,490,488, and 6,895,282. Such known heat treatments have difficulty in targeting the prostate without heating the urethral and rectal walls, which can result in destroying healthy tissue. As a result, monitoring of the temperature of the prostate and surrounding areas is critical to successful procedures. In order to measure accurately the rectal wall temperature and, thereby, monitor the prostate temperature as well, it is necessary that the rectal probe be of sufficient size to press against the rectal wall at the appropriate location. However, such size causes pain and discomfort upon insertion, while after insertion, discomfort is often negligible. Known techniques for monitoring internal temperature, such as those disclosed in U.S. Pat. Nos. 6,348,039, 5,792,070, 5,404,881, 6,475,140, 6,868,290, and 4,046,139, can provide not only poor performance but also discomfort during insertion and complexity of operation.

SUMMARY OF THE INVENTION

The invention generally relates to a probe that is easily inserted into the body of a patient (such as a human or other mammal) and that is comfortable to the patient during insertion, use, and removal, while still effectively engaging an internal wall within the body after insertion into the body. The probe, or at least a portion of the probe, is expandable and collapsible. When collapsed, the probe is insertable into a cavity of the patient's body without causing the patient undue pain or discomfort. After insertion into the cavity, the probe or a portion of the probe can be expanded. After use, the expanded probe or probe portion can be collapsed and easily removed from the patient's body, again without causing the patient undue pain or discomfort. In one embodiment, the probe is a rectal probe and it includes one or more temperature sensors on its expandable/collapsible portion for sensing rectal wall temperature when in place within the rectum of the patient. The temperature of the rectal wall provides a useable and reliable measure of the temperature of the prostate of the patient.

In one illustrative embodiment according to the invention, a rectal probe is easily and comfortably inserted into the rectum of a patient and also expands after insertion to provide efficacious readings within the rectum, such as temperature readings. The rectal probe has an adjustable profile and is designed to be inserted into the rectum or some other body cavity of a human (or other mammal) patient. The probe can include one or more sensors for sensing at least one biological parameter (such as temperature) within the body cavity. The probe can include an elongated shaft with a sensor panel and a resiliently expandable portion that is substantially opposing the sensor panel. An expansion mechanism can be at least partially housed within the elongated shaft. This mechanism is for varying the profile of the probe, and it can include a base plate adjacent to the resiliently expandable portion, a plurality of lever arms pivotally mounted to the base plate, and the sensor panel. An actuating member pivotally connects to the lever arms such that, upon movement of the actuating member, the resiliently expandable portion is selectively collapsed or expanded by the plurality of lever arms pivoting between a minimal profile position parallel or near parallel with the elongated shaft and an expanded profile position with the lever arms being perpendicular or near perpendicular to the elongated shaft. The actuating member can have a plurality of bar links, and the resiliently expandable portion can be made of silicone, latex, and/or nitrile rubber, for example. The resiliently expandable portion can have a varying thickness, and it can have at least one lever arm pivotally mounted to the rigid portion.

In one aspect, the invention generally relates to an adjustable profile probe for insertion in a body cavity to sense a biological parameter. The probe comprises an elongated shaft defining an interior. The elongated shaft includes a proximal end, a closed distal end, a rigid portion, and a resiliently expandable portion substantially opposing the rigid portion. The probe also comprises at least one sensor mounted on the rigid portion for generating a signal corresponding to the biological parameter. The probe also comprises an expansion mechanism that is at least partially housed within the interior. The expansion mechanism includes a base plate, at least one lever arm, and an actuating member. The base plate is disposed adjacent to the resiliently expandable portion. The at least one lever arm includes a first end pivotally mounted to the base plate and a second end disposed adjacent to the rigid portion. The actuating member is pivotally connected to the at least one lever arm and extends toward the proximal end such that, upon movement of the actuating member towards the closed distal end, the resiliently expandable portion expands and, upon movement towards the proximal end, the resiliently expandable portion is allowed to collapse.

Embodiments according to this aspect of the invention can include the following features. The actuating member can include a plurality of bar links. The resiliently expandable portion can be made of silicone, latex, nitrile rubber, or other material(s) that are biocompatible and expandable. The resiliently expandable portion can have a varying thickness. The at least one lever arm can be pivotally mounted to the rigid portion. The rigid portion can be on or near the closed distal end. The at least one sensor can comprise a sensor panel that includes a plurality of the sensors.

In another aspect, the invention generally involves a mechanism for varying a profile of a probe having a sensor panel. The mechanism comprises an expandable portion, at least one arm pivotally mounted to the probe adjacent the expandable portion, and means attached to the at least one arm for moving the at least one arm between a first position, where the profile of the probe is substantially minimized, and a second position, where the at least one arm presses the expandable portion and thereby causes the profile of the probe to enlarge.

Embodiments according to this other aspect of the invention can include the following features. The expandable portion can be substantially opposing the sensor panel. The sensor panel can include at least one temperature sensor. A base plate can have the at least one arm pivotally coupled thereto. The means can be at least one bar link or a screw drive actuator.

In yet another aspect, the invention generally features a mechanism for varying a profile of an elongated rectal probe having a sensor. The mechanism comprises an expandable portion having the sensor mounted adjacent thereto. The mechanism also comprises means, at least partially within the expandable portion, for selectively urging the expandable portion radially outward.

Embodiments according to this other aspect of the invention can include various features. For example, the means can be a linkage mechanism or a flexure member.

In still another embodiment, the invention generally relates to a mechanism for varying a profile of an elongated rectal probe having a sensor. The mechanism comprises an expandable portion, an arm pivotally mounted to the rectal probe adjacent the expandable portion, and a linkage shaft attached to the arm for moving the arm from a first position in which the expandable portion is relaxed and a second position in which the expandable portion is extended.

Embodiments according to this other aspect of the invention can include various features. For example, the expandable portion can have a thickness that varies to determine the profile of the elongated rectal probe in the second position, and a base plate with the arm mounted thereto can be provided.

These and other aspects, features, advantages, and benefits according to the invention are described and shown elsewhere herein.

BRIEF DESCRIPTION OF THE DRAWINGS

The foregoing discussion will be understood more readily from the following detailed description of the disclosed technology, when taken in conjunction with the accompanying drawings in which:

FIG. 3A is an assembled partial cross-sectional side view of the collapsed rectal probe of FIG. 1;

FIG. 3B is an assembled cross-sectional end view of the collapsed rectal probe of FIG. 3A taken along line 3B;

FIG. 4A is an assembled cross-sectional side view of the expanded rectal probe of FIG. 1;

FIG. 4B is an assembled cross-sectional end view of the expanded rectal probe of FIG. 4A taken along line 4B;

FIG. 5A is a cross-sectional side view of the distal end of another rectal probe, in a collapsed state, in accordance with the disclosed technology;

FIG. 5B is an assembled cross-sectional end view of the collapsed rectal probe of FIG. 5A taken along line 5B;

FIG. 6A is a cross-sectional side view of the distal end of the rectal probe of FIG. 5A in an expanded state;

FIG. 6B is an assembled cross-sectional end view of the expanded rectal probe of FIG. 6A taken along line 6B;

DESCRIPTION

Unless otherwise specified, the illustrated embodiments contain exemplary features of varying detail of certain embodiments according to the invention, and therefore, unless otherwise specified, features, components, modules, elements, and/or aspects of the disclosed embodiments can be otherwise combined, interconnected, sequenced, separated, interchanged, positioned, and/or rearranged and still be within the scope of the invention. Additionally, the shapes and sizes of components are exemplary and, unless otherwise specified, generally can be altered without materially affecting or limiting the invention. The term "substantially" can indicate a precise relationship, condition, arrangement, orientation, and/or other characteristic, as well as deviations thereof to the extent that such deviations do not materially impact the disclosed subject matter, as is understood by one of ordinary skill.

In brief and broad overview, the invention generally relates to a profile of a medical device, or a portion of a medical device, that can be adjusted to make it larger or smaller. The disclosed technology can be used to sense a biological parameter such as temperature within a body. An embodiment of a device according to the invention can be inserted into a cavity of the body while the device or a portion of it is in a collapsed state. After insertion into the body, the device or the portion of the device can be expanded or enlarged to, for example, place one or more temperature sensors closer to or in contact with an interior surface of the body cavity to allow temperature readings to be taken. The length and girth of the device or the portion of the device may be modified to allow for readings within the esophagus, ear canal, urethra, sinus passages, and/or other locations within the body of a human patient or the body of another mammal. In one illustrative embodiment, the disclosed technology is used to take temperature, humidity, and/or physiological activity readings like heartbeat, and/or to deliver direct treatment such as heat, a seed, microwave energy, ablation, and/or other types of treatment within the body.

Figure 1:
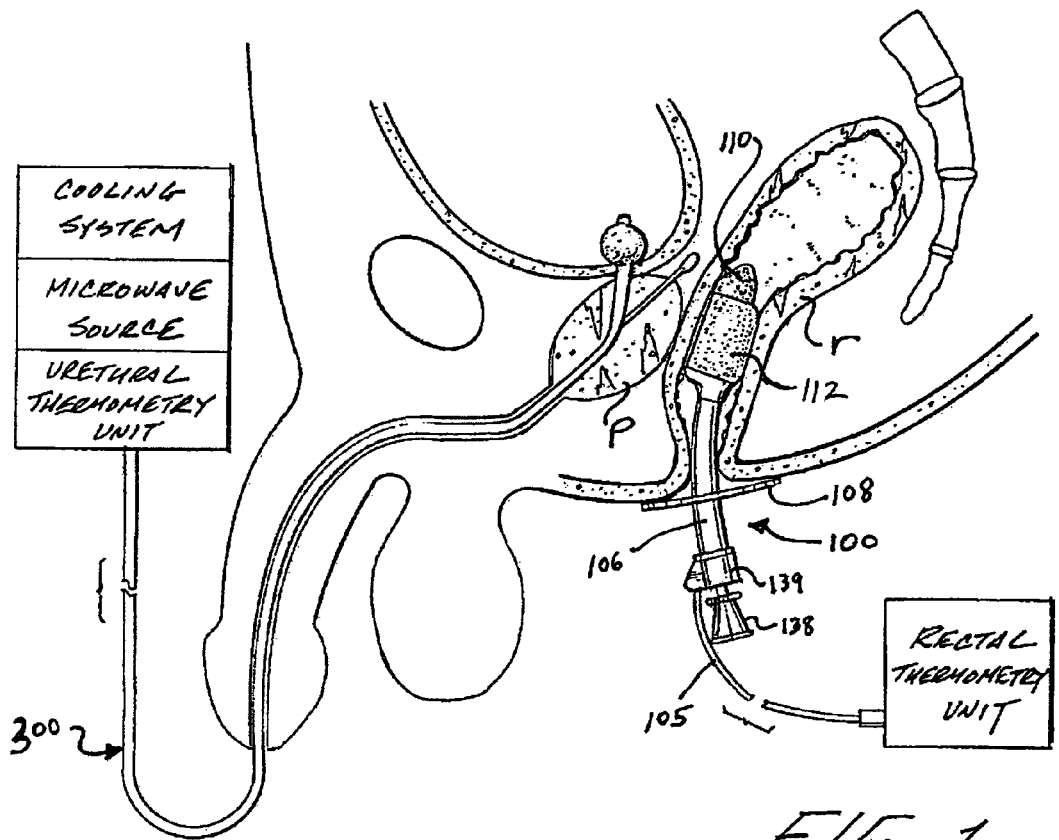
FIG. 1 illustrates a rectal probe for sensing temperature at the prostate in accordance with the subject technology, and in particular a sectional view of a patient having a BPH device and the rectal probe fully disposed in an operational position.

In one embodiment, an adjustable profile probe according to the invention is used to sense prostate temperature during a BPH surgical procedure. An exemplary probe that may be used by inserting it into the rectum of a human (or other mammal) patient to monitor prostate temperature during a BPH procedure is shown in FIG. 1 and referred to generally by the reference numeral 100. A thermal device 300 is inserted into the urethra to perform the BPH procedure. The probe 100 is inserted to place sensors 102 (see FIG. 2) against an area to monitor the temperature in a region. The monitored region can be the prostate "p", and this can be accomplished by inserting the probe 100 in the rectum "r" as shown. When deployed, the medical practitioner aligns the probe 100 such that the sensors 102 are firmly placed against the rectal wall. An expansion mechanism, as described in detail below, presses the sensors 102 against the rectal wall. The probe 100 can be sized and configured to be locked in place with the sensors against the rectal wall near the prostate "p".

The Probe

Figure 2A:
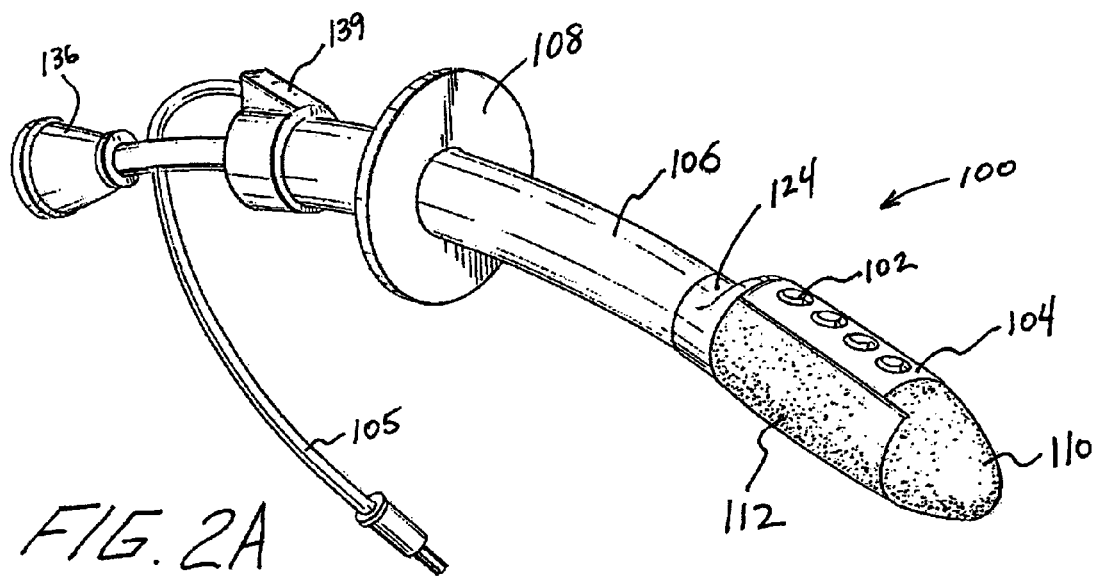
FIG. 2A is a perspective view of the rectal probe of FIG. 1.
Figure 2B:
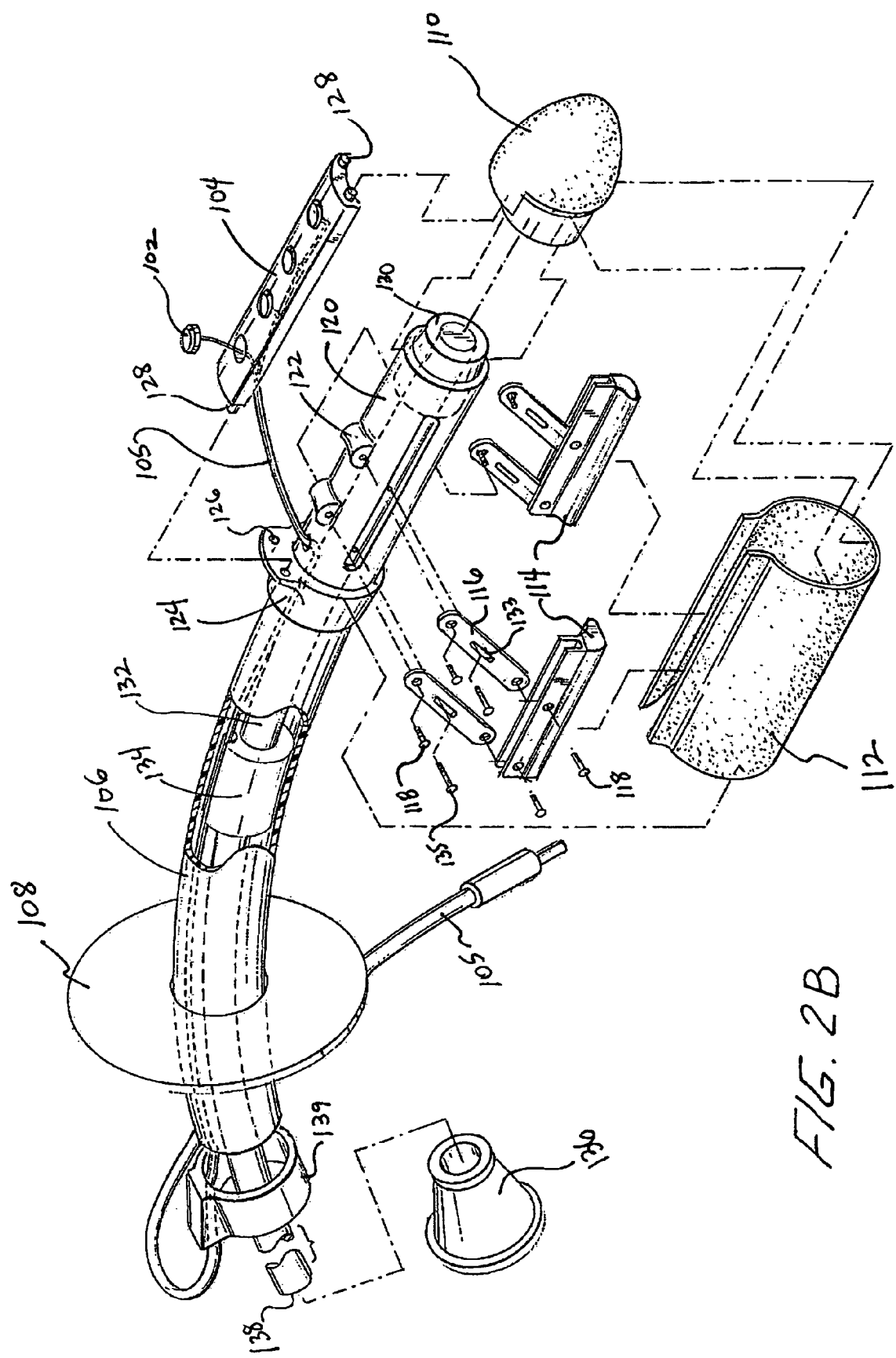
FIG. 2B is an exploded perspective view of the rectal probe of FIG. 1.

Referring now to FIGS. 2A and 2B, perspective and exploded views of the probe 100 are shown, respectively. The sensors 102 mount on a panel 104 that is rigid and engaged to the rectal wall by an expansion mechanism. The sensor panel 104 can have four sensors 102 for providing a plurality of different readings of the rectal wall and, thereby, the prostate "p" as well. Signals from the sensors 104 are carried through leads 105 (only one shown for simplicity) to a rectal thermometry unit for readout for the medical practitioner.

The probe 100 includes an elongated shaft 106 having the sensor panel 104 mounted thereon and defining an interior for housing the expansion mechanism. Although the elongated shaft 106 is flexible (i.e., of a hardness on the Shore A scale of less than about 90) for contouring to the rectum "r", the sensor panel 104 is relatively rigid to effectively press the sensors 102 against the rectal wall. In one embodiment, the length of the elongated shaft 106 is such that upon insertion up to a disk 108 mounted thereon, the sensor panel 104 is in the proximity of the prostate "p". In another embodiment, the elongated shaft 106 includes markings or indicia to allow the medical practitioner to visually read a depth of insertion. A distal end cone 110 of the probe 100 can be frusto-conically shaped to ease insertion or can be some other shape that makes insertion easy for the person inserting the probe 100 and comfortable for the patient receiving the probe 100. The distal end cone 110 is also fabricated from relatively rigid material. The distal end cone 110 also defines holes (not shown) for receiving alignment pins 128 formed on the rigid panel 104 to help retain the rigid panel 104 in place. A collar 130 can couple the distal end cone 110 to the distal end 120 of the probe 100.

The expansion mechanism largely fits within the interior of the elongated shaft 106. The expansion mechanism includes an elastomeric boot portion 112 substantially opposing the sensor panel 104. The elastomeric boot portion 112 can be fabricated from silicone, latex, nitrile rubber, combinations thereof and the like, as would be appreciated by those of ordinary skill. Underneath the elastomeric boot portion 112 are a pair of base plates 114 disposed parallel to the elongated shaft 106. Two pairs of follower arms 116 pivotally mount to each base plate 114 on one end by pins 118. A distal end 120 of the elongated shaft 106 has hubs 122 for pivotally coupling to the other end of the follower arms 116. The distal end 120 is sized and configured to support the rigid portion 104 and follower arms 116. In another embodiment, the follower arms 116 mount directly to the sensor panel 104 such that the elongated shaft 106 is not necessary in the distal end 120.

A shoulder 124 also couples the sensor panel 104 to the elongated shaft 106. The shoulder 124 changes the profile of the probe 100 so that the sensor panel 104 and, thereby, the sensors 102 protrude from probe 100. It is envisioned that the shoulder 124 can be integrally formed with the elongated shaft 106 but many other suitable configurations are possible as would be appreciated by those of ordinary skill in the pertinent art. The shoulder 124 also defines holes 126 for receiving alignment pins 128 formed on the rigid panel.

An elongated coupler linkage 132 extends through the elongated shaft 106 to pivotally couple to slots 133 formed in the follower arms 116. Pins 135 can be free to move within the slots 133. A bushing 134 surrounds the coupler linkage 132 within the elongated shaft 106 to facilitate axial motion of the coupler linkage 132 within the elongated shaft 106. A ferule 136 attaches to the proximal end 138 of the coupler linkage 132 to act as a handle. Similarly, a complimentary ferule 139 attaches to the proximal end 140 of the elongated shaft 106 to also act as a handle for the medical practitioner. The complimentary ferule 139 can form a channel 142 to allow the leads 105 to exit the elongated shaft 106. In another embodiment, the elongated coupler linkage 132 is a screw drive mechanism, one or more bar linkages, or the like, as would be appreciated by those of ordinary skill.

The Collapsed Probe

Referring now to FIGS. 3A and 3B, the probe 100 is shown in cross-sectional side and end view, respectively, in a relaxed state. By relaxed state, the elastomeric boot portion 112 is minimally stressed and the diameter, as represented by arrow 140, of the probe 100 is substantially minimized. To achieve this collapsed condition, the medical practitioner simply extracts the coupler linkage 132 from the elongated shaft 106 by ferule 136. The extraction pulls the follower arms 116 towards the proximal end of the probe 100 whereby the follower arms 116 pivot towards parallel the elongated shaft 106. As the follower arms 116 pivot, the base plates 114 move radially inward and the elastomeric boot portion 112 tracks the motion.

In some embodiments, the natural compressive force of the elastomeric boot portion 112 urges the base plates 114 radially inward. The follower arms 116 can be sized and configured to pivot substantially parallel to the elongated shaft 106. The base plates 114 can be connected as a single arcuate structure. The thickness of the elastomeric boot portion 112 can vary to determine the profile of the probe 100 in the expanded position. Different structure can be used to perform the same function as the coupler linkage 132. For example, alternative linkages such as chain, crank and slider, four-bar, isosceles, quick return, Whitworth, toggle, and/or moving slide linkages could be adapted for use with embodiments according to the invention.

The Expanded Probe

Referring now to FIGS. 4A and 4B, the probe 100 is shown in cross-sectional side and end view, respectively, in an expanded state. In the expanded state, the diameter 140 of the probe 100 is increased. To achieve this expanded condition, the medical practitioner urges the coupler linkage 132 into the elongated shaft 106 by ferule 136. The insertion pushes the follower arms 116 towards the proximal end of the probe 100 whereby the follower arms 116 pivot towards perpendicular the elongated shaft 106. As the follower arms 116 pivot perpendicularly, the base plates 114 move radially outward and the boot portion 112 expands.

In another embodiment, detents or other well-known position locking mechanisms are utilized on the probe 100 and between the elongated shaft 106 and coupler linkage 132 to allow the medical practitioner to easily alternate between expanded and collapsed conditions. In still another embodiment, the coupler linkage 132 is relatively stiff and segmented into various coupled portions to allow for conforming to a body opening.

Another Probe

Referring now to FIGS. 5A and 5B, another embodiment of the probe of the present invention is indicated generally by the reference numeral 200. As will be appreciated by those of ordinary skill in the pertinent art, the probe 200 utilizes similar principles to the probe 100 described above. Accordingly, like reference numerals preceded by the numeral "2" instead of the numeral "1", are used to indicate like elements whenever possible. The primary difference of probe 200 is that rather than having a coupler linkage extending through the elongated shaft 206, an inner shaft 207 inserts therein. The inner shaft 207 has a leaf spring 209 mounted on the distal end 211 thereof. The elongated shaft 206 forms an aperture 207 adjacent the elastomeric boot portion 212. When the inner shaft 207 is pulled away from the distal end cone 210, the leaf spring 209 is compressed substantially flush against the inner shaft 207 within the elongated shaft 206. As a result, the profile of the probe 200 is negligibly affected.

Referring now to FIGS. 6A and 6B, when the inner shaft 207 is urged toward the distal end cone 210, the leaf spring 209 expands through aperture 207 to press radially outward against the elastomeric boot portion 212. As a result, the diameter of the probe 200 is expanded. In another embodiment, the leaf spring 209 extends beyond the distal end 211 of the inner shaft 207 such that the compressive force generated against the distal end cone 210 bows the leaf spring 209 radially outward against the elastomeric boot portion 212.

Implantation of the Probe

Figure 7:
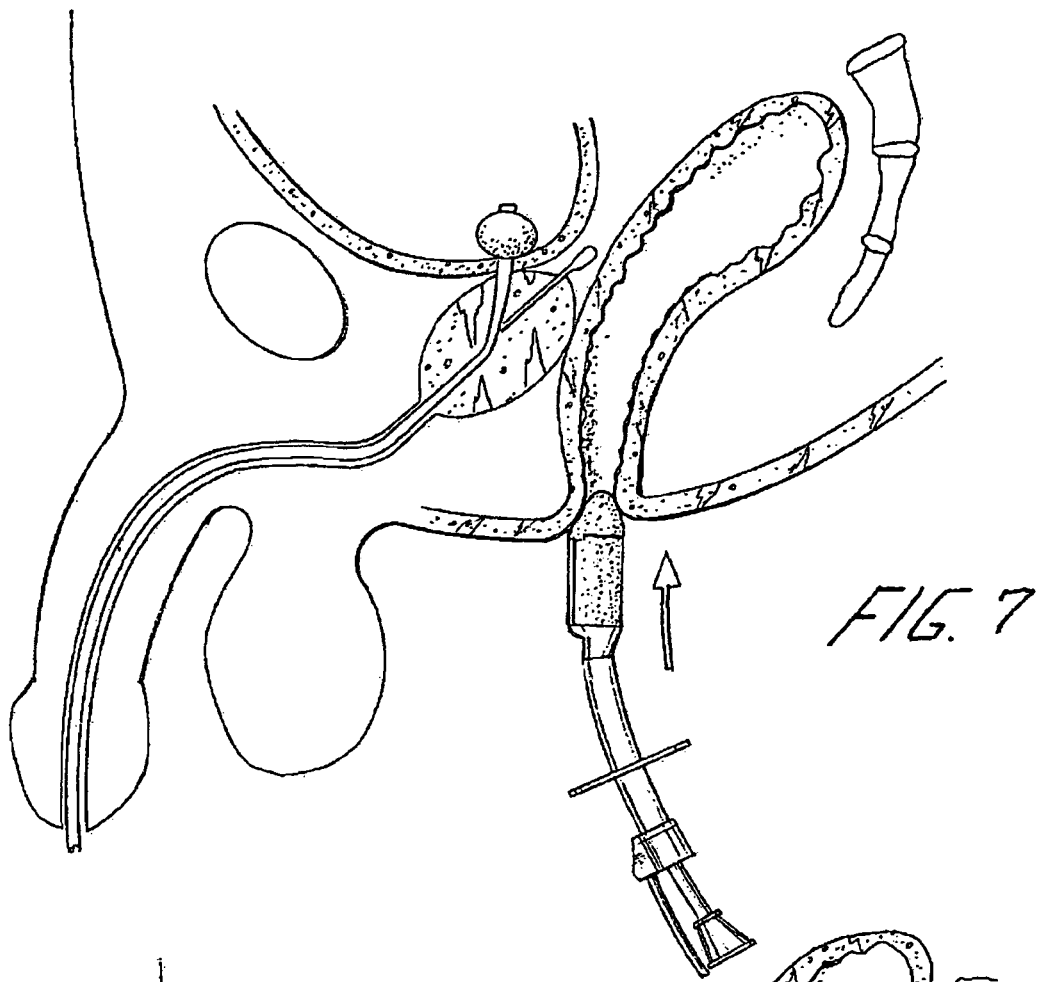
FIG. 7 is an assembled view of the rectal probe of FIG. 1 in preparation for insertion into a patient.
Figure 8:
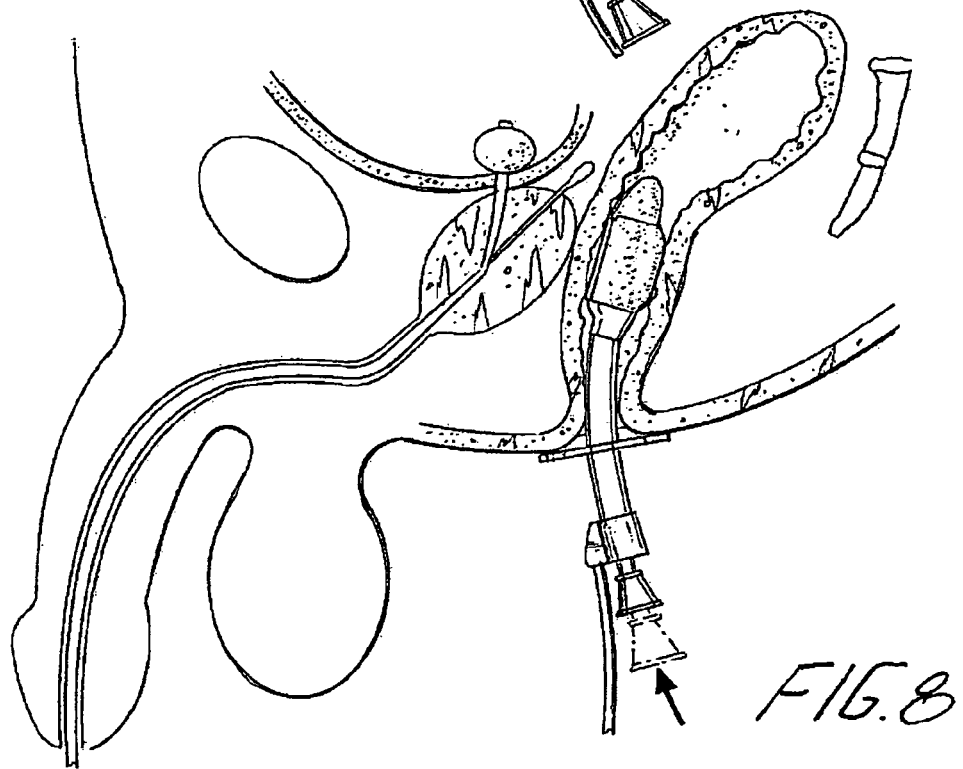
FIG. 8 is an assembled view of the rectal probe of FIG. 1 being expanded in a patient after insertion.

Referring now to FIGS. 7 and 8, the probe 100 being deployed in the rectum "r" of a patient is illustrated. In FIG. 7, the probe 100 is placed in a relaxed or minimal profile state by retracting the coupler linkage 132. A lubricant can be applied to the distal end cone 110 and otherwise as necessary to ease insertion. The medical practitioner inserts the relaxed probe 100 into the rectum "r" until the disk 108 reaches the rectum "r" as shown in FIG. 8. As a result, the probe 100 places the sensor panel 104 and, thereby, the sensors 102 in the portion of the rectum "r" near the prostate "p".

Upon insertion to the appropriate depth, the medical practitioner urges the coupler linkage 132 towards the distal end cone 110 to activate the expansion mechanism. As the follower arms 116 pivot, the base plates 114 are urged radially outward and the elastomeric boot portion 112 expands outward such that the cross-sectional dimension of the probe 100 is increased. The expansion of the diameter of the probe 100 locks the probe 100 in place with the sensors 102 pressed against the rectal wall as shown in FIG. 1. Upon deployment, the probe 100 directly senses the temperature of the rectal wall in a plurality of locations and indirectly monitors the temperature of the surrounding area, such as the prostate.

The functions of various elements described herein may, in some embodiments, be carried out by more or fewer elements, including by a single element. Similarly, in some embodiments, any functional element may perform fewer, or different, operations than those described with respect to the illustrated embodiment. Also, functional elements (e.g., linkages, shafts, couplers, elastic portions, and the like) shown as distinct for purposes of illustration may be incorporated within other functional elements in a particular implementation. It is also envisioned that the disclosed probes may be adapted to monitor a plurality of parameters in any body orifice.

While certain illustrative embodiments according to the invention are disclosed herein, the invention is not limited to or by the disclosed embodiments. Also, various changes and/or modifications can be made to the disclosed embodiments without departing from the spirit or scope of the invention.

What is claimed is:

1. A mechanism for varying a profile of an elongated rectal probe having a sensor, comprising:
   an expandable portion;
   a plurality of lever arms pivotally mounted to the rectal probe adjacent the expandable portion, the sensor protruding through a rigid sensor panel and mounted to a portion of the rectal probe separate from the expandable portion at a fixed radial distance from a longitudinal axis defined by the elongated rectal probe; and
   a linkage shaft attached to the plurality of lever arms for moving the arms from a first position in which the expandable portion is relaxed and a second position in which the expandable portion is extended, the sensor being at the fixed radial distance when the expandable portion is relaxed and when the expandable portion is extended, the rigid sensor panel mounted to the elongated rectal probe by a shoulder configured to raise the profile of the sensor panel with respect to the elongated rectal probe to press the sensor against a wall of an organ when the expandable portion is extended within a body of a patient.

2. The mechanism of claim 1 wherein the expandable portion has a thickness that varies to determine the profile of the elongated rectal probe in the second position.

3. The mechanism of claim 1 further comprising a base plate with at least one of the plurality of lever arms mounted thereto.

4. An adjustable profile probe for insertion in a body cavity to sense a biological parameter, comprising:
   an elongated shaft defining an interior, the elongated shaft including a proximal end, a closed distal end, a rigid portion, and a resiliently expandable portion substantially opposing the rigid portion;
   at least one sensor mounted on the rigid portion for generating a signal corresponding to the biological parameter, the at least one sensor protruding through a sensor panel; and
   an expansion mechanism at least partially housed within the interior, the expansion mechanism separate from the rigid portion, the expansion mechanism including:
      a base plate adjacent to the resiliently expandable portion;
      a plurality of lever arms including a first end pivotally mounted to the base plate and a second end adjacent to the rigid portion; and
      an actuating member pivotally connected to the plurality of lever arms and extending toward the proximal end such that, upon movement of the actuating member towards the closed distal end, the resiliently expandable portion expands and, upon movement towards the proximal end, the resiliently expandable portion is allowed to collapse, the at least one sensor being disposed at a fixed radial distance from a longitudinal axis defined by the elongated shaft when the expandable portion both expands and collapses, the sensor panel mounted to the elongated shaft by a shoulder configured to raise the profile of the rigid sensor panel with respect to the elongated shaft to press the sensor against a wall of an organ when the expandable portion is expanded within a body of a patient.

5. The probe of claim 4 wherein the at least one sensor is fixedly mounted relative to the elongated shaft.

6. The probe of claim 4 wherein the actuating member includes a plurality of bar links.

7. The probe of claim 4 wherein the resiliently expandable portion is fabricated from a material selected from the group consisting of silicone, latex, nitrile rubber, and combinations thereof.

8. The probe of claim 7 wherein the resiliently expandable portion has a varying thickness.

9. The probe of claim 4 wherein at least one of the plurality of lever arms is pivotally mounted to the rigid portion.

10. The probe of claim 4 wherein the rigid portion is near the closed distal end.

11. The probe of claim 4 wherein the rigid portion is on the closed distal end.

12. The probe of claim 4 wherein the sensor panel includes a plurality of sensors.

13. A mechanism for varying a profile of a probe, comprising:
   an expandable portion;
   a plurality of lever arms pivotally mounted to the probe adjacent the expandable portion;
   at least one temperature sensor protruding through a rigid sensor panel; and
   means attached to the plurality of lever arms for moving the plurality of lever arms between:
   (a) a first position where the profile of the probe is substantially minimized, the rigid sensor panel located at a radial distance from a longitudinal axis of the probe when the lever arms are in the first position; and
   (b) a second position where the at least one arm presses the expandable portion and thereby enlarges the profile of the probe, the rigid sensor panel located at the same radial distance from the longitudinal axis of the probe when the lever arms are in the second position as when the lever arms are in the first position, the rigid sensor panel mounted to the probe by a shoulder configured to raise the profile of the sensor panel with respect to the probe to press the at least one sensor against a wall of an organ when the expandable portion is enlarged within a body of a patient.

14. The mechanism of claim 13 wherein the expandable portion is substantially opposing the rigid sensor panel.

15. The mechanism of claim 13 further comprising a base plate with at least one of the plurality of lever arms pivotally coupled thereto.

16. The mechanism of claim 13 wherein the means is at least one bar link.

17. The mechanism of claim 13 wherein the means is a screw drive actuator.

* * * * *